United States Patent [19]
Mann et al.

[11] Patent Number: 5,167,809
[45] Date of Patent: Dec. 1, 1992

[54] CHROMATOGRAPHY SYSTEM

[75] Inventors: Anthony F. Mann, Wiltshire, England; Vincenzo Vassarotti, Bugnaux-sur-Rolle, Switzerland

[73] Assignee: Amicon Ltd., Gloucestershire, United Kingdom

[21] Appl. No.: 757,868

[22] Filed: Sep. 11, 1991

[30] Foreign Application Priority Data

Sep. 19, 1990 [GB] United Kingdom ............... 9020453

[51] Int. Cl.$^5$ ............................................. B01D 15/08
[52] U.S. Cl. ............................ 210/198.2; 210/656; 210/189; 55/386
[58] Field of Search ................ 210/656, 189, 198.2, 210/238, 241, 244, 246, 464, 465; 55/386; 422/70

[56] References Cited

U.S. PATENT DOCUMENTS

| | | | |
|---|---|---|---|
| 467,604 | 1/1892 | Baird | 210/244 |
| 2,087,157 | 7/1937 | Lind | 210/189 |
| 2,456,524 | 12/1948 | Meincke | 210/244 |
| 3,250,395 | 10/1966 | Blume | 210/198.2 |
| 3,474,908 | 10/1969 | Catravas | 210/198.2 |
| 3,483,986 | 12/1969 | Wright | 210/198.2 |
| 4,689,147 | 8/1987 | Leoncavallo | 210/244 |
| 5,021,162 | 6/1991 | Sakamoto | 210/198.2 |

FOREIGN PATENT DOCUMENTS

| | | | |
|---|---|---|---|
| 60-142251 | 7/1985 | Japan | 210/198.2 |
| 61-294361 | 12/1986 | Japan | 210/198.2 |

Primary Examiner—Ernest G. Therkorn
Attorney, Agent, or Firm—Margit Maus; William L. Baker

[57] ABSTRACT

A chromatography system comprises a chromatography column 1 consisting of a column tube 7 having end flanges 19 and 27 at its lower and upper ends, supporting an upper end cap 3 carrying a piston rod 9 and a piston 11. The system further comprises a container 20 for the separation media used in the chromatography column, this container having a neck ring 24 of injection moulded construction with a mouth end of a bag 22 embedded therein.

15 Claims, 3 Drawing Sheets

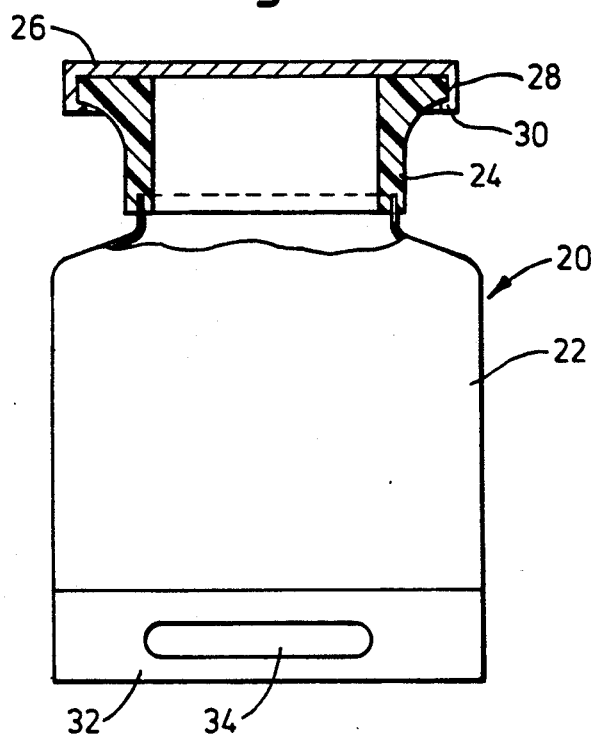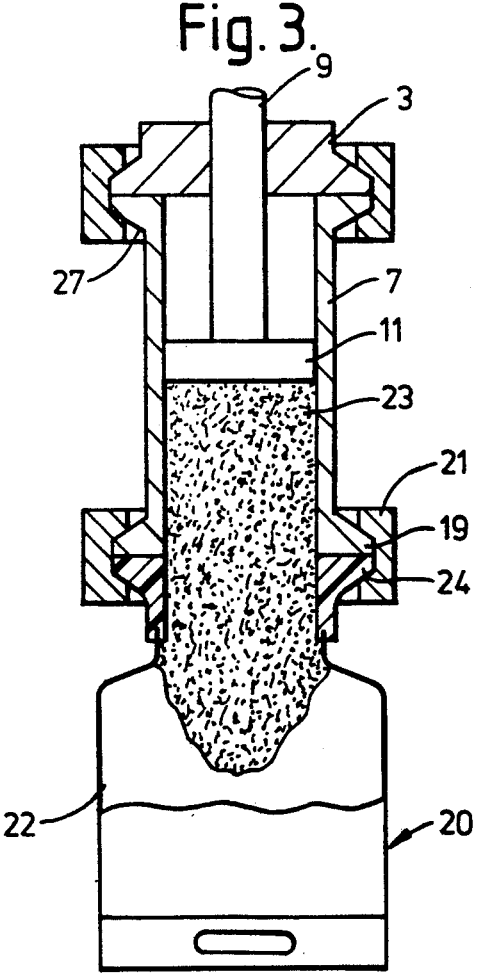

CHROMATOGRAPHY SYSTEM

The present invention relates to a chromatography system, and in particular to a system which enables a chromatography column to be charged with separation media and drained of separation media on unpacking of the column, substantially without contamination of the media undergoing introduction or removal, and substantially without risk of exposure of operators to the separation media which may, on unpacking of the column, have become contaminated with a product separated out during the chromatography process.

The design of chromatography columns varies according to the end use, and it is known for the size range of such columns to extend from, on the one hand, laboratory scale columns which enable analysis of relatively small samples of products by chromatography separation techniques to be carried out to, on the other hand, factory scale columns where the separation effect of the chromatography technique may be used for purifying a product by extracting certain of its constituents by the separation media in the chromatography bed, or recovery of a desirable constituent of input material by separating out that constituent from the material passing through the bed and subsequently recovering it by washing the separation media of the bed.

All of these possibilities require safe handling of the separation media during packing, unpacking and re-packing of the column, and additionally in certain circumstances there may be a need to protect the operators from contact with the separation media.

It is an object of the present invention to provide a chromatography system which enables a chromatography column to be packed and re-packed with separation media, while containing the separation media during the packing operation before introduction into the column and during the unpacking operation after discharge from the column.

Accordingly, the present invention provides a chromatography system comprising a column tube having end flanges for releasable attachment of end caps of the chromatography column, and at least one container having a neck formation adapted to engage said end flanges for attachment of the container to the ends of the column tube, allowing discharge of separation media from the column into such a container upon unpacking, and from such a container into the column upon re-packing.

DESCRIPTION OF THE DRAWINGS

In order that the present invention may more readily be understood the following description is given, merely by way of example, with reference to the accompanying drawings, in which:

FIG. 2 is a partial sectional view of a container forming part of the chromatography system in accordance with the present invention;

FIG. 3 is a schematic partial sectional view showing the chromatography column during discharge of the separation media upon unpacking of the bed.

DESCRIPTION OF THE PREFERRED EMBODIMENTS

Figure 1:
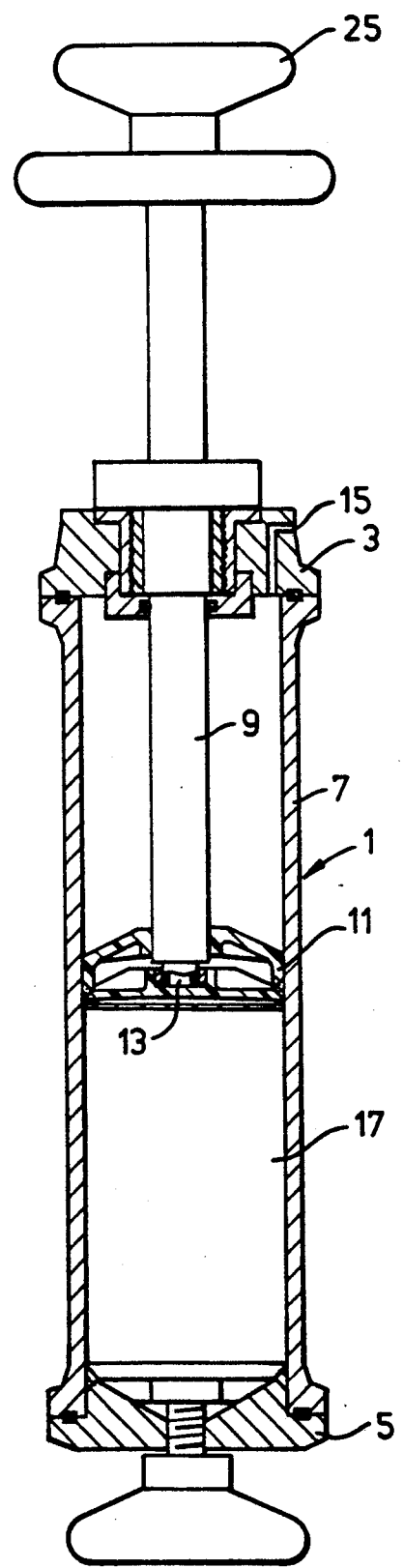
FIG. 1 is a sectional view of a chromatography column in use during chromatography separation, but without the separation media in the bed illustrated.
Figure 4:
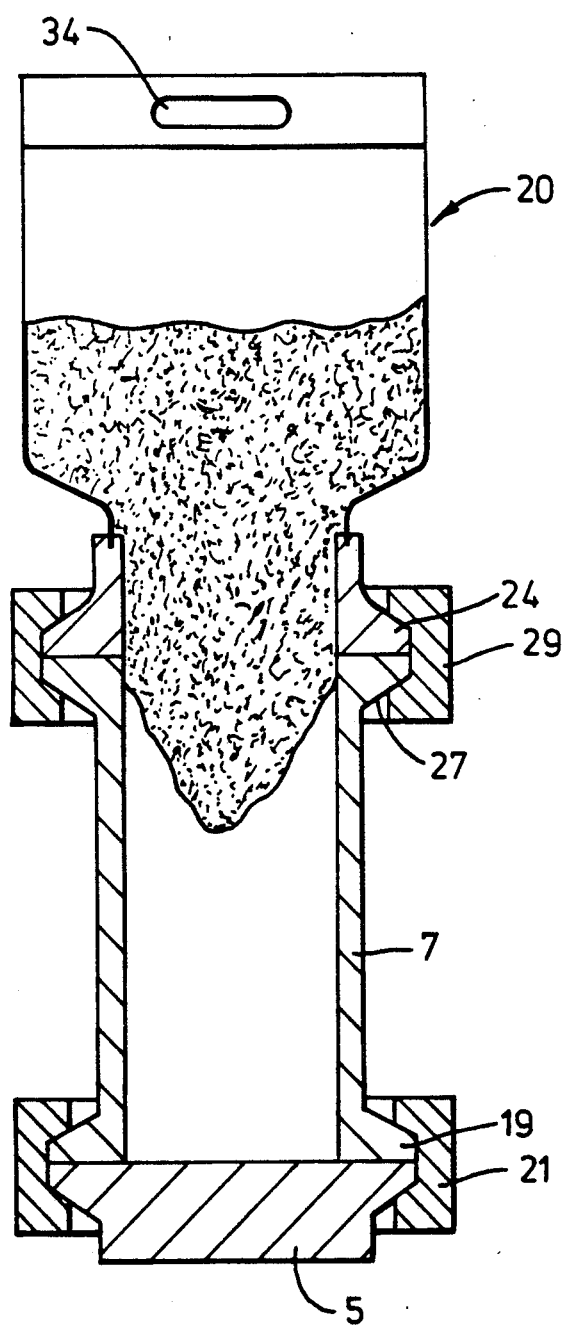
FIG. 4 is a further schematic view showing introduction of separation media into the chromatography column, normally after cleansing of the separation media by washing following the previous chromatography separation operation.

FIG. 1 shows the chromatography column 1 as comprising an upper end cap 3 and a lower end cap 5, to be held to respective upper and lower flanges of the column tube 7 by means of clamps which are shown in FIGS. 3 and 4. The preferred form for these clamps is a chain clamp, constructed in the manner of a large-link bicycle chain with clamp pads carried by links of the chain and arranged such that the chain can be wound once around the mating flanges of the end cap and the associated end of the column tube, and then the ends of the chain can be fastened together. Such chain clamps are known in the art. Alternatively, a C-clamp can be used.

The column further comprises a piston rod 9 carrying a piston 11 which serves as upper end cell for the chromatography bed and through which the medium to be separated can pass, after introduction through the hollow interior 13 of the piston rod 9. The preferred construction of the piston of this bed is described and claimed in our simultaneously filed British Patent Application No. 9020450.4.

The piston rod 9 can be clamped by a friction clamp or adjusted by a screw action, by virtue of the manner in which the piston rod is mounted in the upper end cap 3. This preferred mechanism is described and claimed in our simultaneously filed British Patent Application No. 9020451.2.

The upper end cap furthermore preferably includes a pneumatic inlet 15 to allow pneumatic driven movement of the piston 11, as is described in our said British Patent Application No. 9020451.2.

When the bed is to be unpacked, the clamp (not shown) holding the lower end cap 5 in place is removed allowing the end cap 5 then to be withdrawn from the bottom of the column. The chromatography media in the bed space 17 can then be discharged, preferably with the aid of pneumatic pressure applied through the inlet 15 after release of the friction clamp on the piston rod 9. This allows the piston 11 to be displaced downwardly to displace the separation media in turn from the bed space 17 into a container shown in more detail in FIGS. 2 to 4.

Upon re-packing of the bed, the lower end plate 5 will have been replaced and clamped in position by its appropriate clamp, and the upper end cap 3 will have been removed by release of its clamp, and by withdrawal of the piston 11 and piston rod 9 from the interior of the column tube 7. This allows the separation media to be introduced, either by pouring into the bed in the case of fresh separation media of a relatively easily handled form, or by introduction from a container of the type just described for use in receiving the discharged separation media on unpacking; this re-charging operation will be described later with reference to FIG. 3.

The container 20 referred to above is illustrated in FIG. 2 and comprises a bag 22 of relatively flexible film material capable of withstanding the action of solvents or other hazardous chemicals found in either the separation media or the material being separated. The film is preferably transparent. Convenient materials for use for forming the container 20 include polypropylene and polymethyl pentene. Polymethyl pentene is particularly preferred as having the desired mechanical strength, chemical resistance, and transparency for use in chromatography bed packing and unpacking. This can be extruded as a film through a suitable die. Polymethyl pentene is available from Mitsui Petrochemical Company of Japan under the Trade Mark "TPX".

The mouth end of the bag 22 is embedded in a plastic neck collar 24 which is injection moulded around the mouth of the bag and will also preferably be of a material capable of withstanding the mechanical and chemical attacks which the bag itself must tolerate. Again polymethyl pentene and polypropylene are suitable materials for the neck collar 24.

As can be seen by reference to FIGS. 3 and 4, the neck collar 24 cooperates with the end flanges of the column tube 7 to allow the neck collar to be clamped to either the lower column tube flange 19 or the upper column tube flange 27, depending on whether the bed is being unpacked or repacked, by use of the same C clamps or chain clamps described above with reference to holding the end caps 3 and 5 in place.

Finally, the neck collar is provided with a snap on cover 26 to allow the separation media contained in the bag 22 to be free from contact with fresh atmospheric air. The snap-on action of the cover 26 is achieved by virtue of its peripheral skirt 28 having a radially inwardly extending but deformable flange 30 to snap under the radially outer rim of the neck collar 24.

At the closed end of the bag, its opposing walls are sealed together to form a fin 32, and a hand-hold aperture 34 may be formed in this fin, to allow the bag to be transported readily and to assist manipulation of the bag in the column re-packing operation.

The operation of unpacking the column of FIG. 1 will now be described with reference to FIG. 3. Where necessary the chromatography column may be placed, still in a sealed condition, in a suitable containment chamber which allows the separation media to be discharged under safe conditions.

Either inside such a containment chamber, or in the working room where the chromatography operation has just been carried out, the lower end cap 5 of the chromatography column is removed by unfastening the clamp 21 holding it in place, and instead the neck collar 24 of the container 20 is clamped in place on the lower end flange 19 of the column by means of the same clamp 21.

During this operation the container 20 will be empty and its cover 26 will have been previously removed.

The state of the separation media 23 in the column will be that of a relatively self-supporting mass which has been packed in place by virtue of both the binding action of the liquid which has just passed through the column, and the fact that the column may well have been pressurised during the chromatography operation. It is therefore necessary to lower the piston 11 by driving the piston rod 9 downwardly to expel the separation media 23 into the container 20. If desired this may be achieved manually, but it is preferred to expel the separation media pneumatically by releasing the friction clamp and applying pneumatic pressure through the inlet 15 to drive the piston downwardly thereby expelling the separation media 23 from the column and into the container 20.

Upon completion of the discharge stroke of the piston 11 to arrive at the bottom end of the column tube 7, either that stroke can be terminated or, by virtue of the mating action of the container neck column 24 on the lower end flange 19 of the column, the stroke may be continued in order to drive the separation media clear of the neck collar 24, positively into the bag portion 22 of the container 20. If this latter additional stroke has been effected, the piston 11 will need to be retracted before the container 20 can be removed.

The clamp 21 is then released and the neck collar 24 of the container is withdrawn and the snap-on cover 26 is then snapped in place to seal the separation media 23 within the container 20.

If the chromatography column is to be re-used without sterilisation, then the bottom end cap 5 is replaced in position and the clamp 21 fastened to hold it in place. Otherwise, the various constituent parts of the column 1 may be sterilised before re-assembly prior to the next packing operation.

Likewise the media may be sterilised in an autoclave while still contained in the container 20, provided the bag is made of a material able to resist the temperature used. Such a material would be polymethyl pentene or polypropylene.

When re-packing is required using media already contained in a container 20, the column 1 on which the lower end cap 5 has already been replaced, as shown in FIG. 4, has its upper end cap 3 and piston structure removed and then, after removal of the snap-on cover 26 from the neck collar 24 of the container 20, the container is secured in place by clamping of its neck collar 24 to the upper end flange 27 of the column tube 7, using the upper clamp 29.

In order to arrive at this situation the container 20 may be lifted into position using the hand-hold aperture 34 as a means of supporting the bag.

Once the clamp 29 has been fastened the upper end of the bag can be pushed down manually, again by grasping the hand-hold aperture 34, to expel the separation media from the container 20 into the interior of the chromatography column tube 7. Once all or substantially all of the separation media is in the column, preferably with all of it below the neck collar 24, the clamp 29 can be unfastened in order to allow the neck collar 24 of the container 22 to be removed from the upper flange 27, and then to allow replacement of the upper end cap 3 with its piston 11 and piston rod 9.

Once the container neck collar 24 has been removed, the snap-on cover 26 is replaced on the container to keep its interior sterile, and thereafter, once the upper end cap 3 and its piston and piston rod structure have been replaced, the piston can be traversed downwardly to drive the separation media down against the lower end cap 5, or more properly against the lower end cell carried thereby, and the bed may if necessary be pressurised before start of the next separation operation by introduction of in-feed material into the bed through the piston 11.

We claim:

1. A chromatography system comprising a column tube having end flanges for releasable attachment of end caps of the chromatography column, and at least one container having a neck formation adapted to engage said end flanges for attachment of the container to the ends of the column tube, allowing discharge of separation media from the column into such a container upon unpacking, and from such a container into the column upon re-packing, wherein said container includes a neck collar having a form suitable for clamping to the neck flanges of the column tube using clamps which otherwise clamp said end caps in place and wherein said container further comprises a bag having its mouth defined by said neck collar, and piston discharge means for discharging media from said column.

2. The chromatography system of claim 1, wherein said container further comprises a flexible bag having its mouth defined by said neck collar.

3. The chromatography system of claim 2, wherein said bag has a mouth end embedded in an axially extending sleeve portion of said neck collar.

4. The chromatography system of claim 3, wherein said bag has at its closed end a fin defined by superposition and mutual welding of the opposing walls of the bag, said fin including means allowing the bag to be lifted by grasping the fin.

5. The chromatography system of claim 4, wherein said grasping means includes a hand-hold aperture formed in said fin.

6. The chromatography system of claim 2, wherein said bag has at its closed end a fin defined by superposition and mutual welding of the opposing walls of the bag, said fin including means allowing the bag to be lifted by grasping the fin.

7. The chromatography system of claim 6, wherein said grasping means includes a hand-hold aperture formed in said fin.

8. The chromatography system of claim 6, wherein said bag is formed of extruded polymethyl pentene film and said neck collar is injection moulded around the open end of said bag of extruded polymethyl pentene film.

9. The chromatography system of claim 6, wherein said bag is formed of extruded polypropylene film and said neck collar is injection moulded around the open end of said bag of extruded polypropylene film.

10. The chromatography system of claim 1 further comprising a snap-on cover adapted to close said neck collar.

11. The chromatography system of claim 1, wherein said container is formed of a material which is transparent and is resistant to chemical attack by solvents.

12. The chromatography system of claim 11, wherein said container is formed of a material capable of being sterilised in an autoclave.

13. The chromatography system of claim 12, wherein said material is polymethyl pentene.

14. The chromatography system of claim 1, wherein said container is formed of a material capable of being sterilised in an autoclave.

15. The chromatography system of claim 1, wherein said container is formed of polypropylene.

* * * * *